United States Patent
Arumugam et al.

(10) Patent No.: US 7,183,431 B1
(45) Date of Patent: Feb. 27, 2007

(54) DIHYDROXY AROMATIC COMPOUNDS AND METHODS FOR PREPARATION

(75) Inventors: Nagarajan Arumugam, Tamilnadu (IN); Radhakrishna As, Karnataka (IN); Jan Pleun Lens, N-Brabant (NL); Tilak Raj, Karnataka (IN); Binod Sahoo, Orissa (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/289,215

(22) Filed: Nov. 29, 2005

(51) Int. Cl.
*C07C 233/05* (2006.01)
*C07C 231/02* (2006.01)

(52) U.S. Cl. ..................... 564/158; 564/133
(58) Field of Classification Search ............... 564/158, 564/133
See application file for complete search history.

(56) References Cited

U.S. PATENT DOCUMENTS

| | | | | |
|---|---|---|---|---|
| 2,772,162 A | * | 11/1956 | Salminen et al. | 430/384 |
| 2,865,751 A | * | 12/1958 | George et al. | 430/503 |
| 3,856,748 A | * | 12/1974 | Dexter et al. | 524/222 |
| 4,577,042 A | * | 3/1986 | Collins et al. | 564/158 |
| 5,130,454 A | * | 7/1992 | Hickmann et al. | 558/268 |
| 5,130,481 A | * | 7/1992 | Khanna et al. | 564/157 |
| 5,157,066 A | * | 10/1992 | Shoji et al. | 524/220 |

* cited by examiner

*Primary Examiner*—Shailendra Kumar

(57) ABSTRACT

A dihydroxy aromatic compound having a Formula (I),

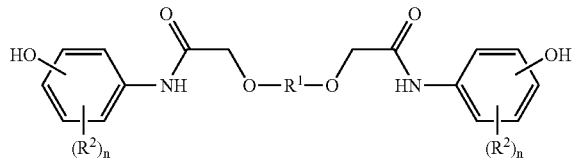

(I)

wherein $R^1$ is a $C_6$–$C_{60}$ aromatic divalent functionality, $R^2$ at each occurrence, can be the same or different and is independently at each occurrence selected from the group consisting of a cyano functionality, a nitro functionality, a halogen, an aliphatic functionality having 1 to 10 carbons, a cycloaliphatic functionality having 3 to 10 carbons and an aromatic functionality having 6 to 10 carbons, and "n" is an integer having a value of 0 to 4.

22 Claims, No Drawings

DIHYDROXY AROMATIC COMPOUNDS AND METHODS FOR PREPARATION

BACKGROUND

This disclosure generally relates to dihydroxy aromatic compounds. More particularly the disclosure relates to dihydroxy aromatic compounds and methods for preparing the compounds.

Dihydroxy aromatic compounds are generally known to be useful in the preparation of polycarbonates that exhibit exceptional properties like high glass transition temperature (Tg), high refractive index (RI), chemical resistance, and barrier properties. Materials having higher Tg and higher RI properties are in great demand for use in various applications like automotives and optical media.

Accordingly, there is a continuing need for new compounds that will provide polymers with better chemical resistance and at the same time retain high Tg values to enable their use in forming a gamut of articles.

BRIEF SUMMARY

Disclosed herein are dihydroxy aromatic compounds having Formula (I),

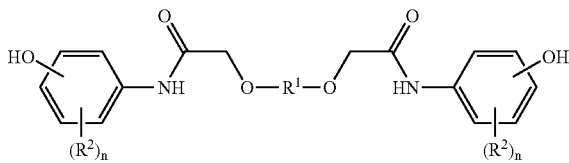

(I)

wherein $R^1$ is an aromatic functionality having 6 to 60 carbons, $R^2$ at each occurrence can be the same or different and is independently at each occurrence selected from the group consisting of a cyano functionality, a nitro functionality, a halogen, an aliphatic functionality having 1 to 10 carbons, a cycloaliphatic functionality having 3 to 10 carbons and an aromatic functionality having 6 to 10 carbons and further wherein "n" is an integer having a value of 0 to 4.

In another embodiment a process for producing the dihydroxy aromatic compounds of Formula (I) comprises reacting a compound of Formula (III) with a compound of Formula (IV) in the presence of a first base to produce a compound of Formula (V)

HO—$R^1$—OH (III)

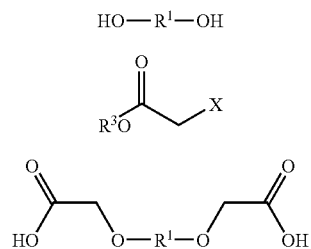

(IV)

(V)

reacting the compound of Formula (V) in the presence of a first catalyst with a halogenating agent to provide the corresponding diacid halide having Formula (VI)

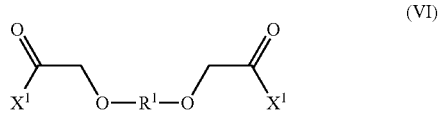

(VI)

and reacting the compound of Formula (VI) with a compound of Formula (VII) in the presence of a second base to produce a compound of Formula (I)

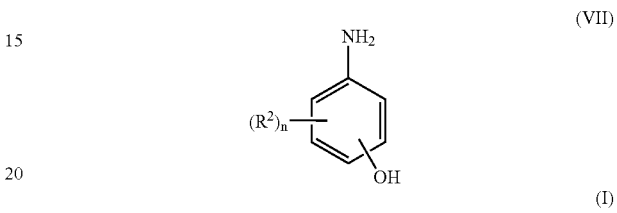

(VII)

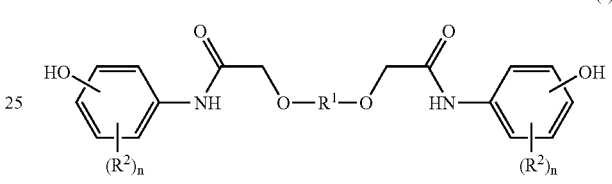

(I)

wherein $R^1$ is an aromatic functionality having 6 to 60 carbon atoms, $R^2$ at each occurrence can be the same or different and is independently at each occurrence selected from the group consisting of a cyano functionality, a nitro functionality, a halogen, an aliphatic functionality having 1 to 10 carbons, a cycloaliphatic functionality having 3 to 10 carbons and an aromatic functionality having 6 to 10 carbons, X and $X^1$ are independently at each occurrence a halogen, $R^3$ is selected from the group consisting of a hydrogen and an aliphatic functionality having 1 to 10 carbons, and "n" is an integer having a value of 0 to 4.

In one embodiment a composition comprises a dihydroxy aromatic compound having a Formula (I),

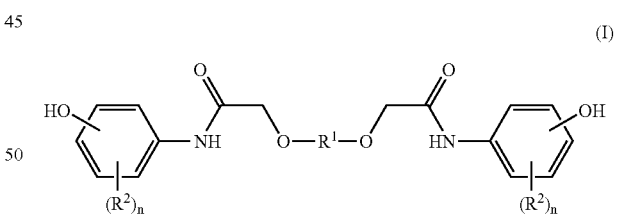

(I)

wherein $R^1$, $R^2$ and "n" are defined as above.

DETAILED DESCRIPTION

Disclosed herein are dihydroxy aromatic compounds and methods for preparing these compounds. These compounds may find applications as monomers in the preparation of polymers, especially in the preparation of polymers having chemical resistance and high Tg.

The singular forms "a", "an" and "the" include plural referents unless the context clearly dictates otherwise. All ranges disclosed herein are inclusive and combinable (for example ranges of "up to 25 wt %, with 5 wt % to 20 wt % desired," is inclusive of the endpoints and all intermediate values of the ranges of "5 wt % to 25 wt %").

The modifier "about" used in connection with a quantity is inclusive of the stated value and has the meaning dictated by the context (for example, includes the degree of error associated with measurement of the particular quantity).

Unless otherwise specified, the term "cycloaliphatic functionality" designates cyclic aliphatic functionalities having a valence of at least one and comprising an array of atoms which is cyclic but which is not aromatic. A "cycloaliphatic functionality" may comprise one or more noncyclic components. For example, a cyclohexylmethyl group ($C_6H_{11}CH_2$) is a cycloaliphatic functionality, which comprises a cyclohexyl ring (the array of atoms which is cyclic but which is not aromatic) and a methylene group (the noncyclic component). The cycloaliphatic functionality may include heteroatoms such as nitrogen, sulfur, selenium, silicon and oxygen, or may be composed exclusively of carbon and hydrogen. For convenience, the term "cycloaliphatic functionality" is defined herein to encompass a wide range of functional groups such as alkyl groups, alkenyl groups, alkynyl groups, haloalkyl groups, conjugated dienyl groups, alcohol groups, ether groups, carboxylic acid groups, acyl groups (for example carboxylic acid derivatives such as esters and amides), amine groups and nitro groups. For example, the 4-methylcyclopent-1-yl group is a $C_6$ cycloaliphatic functionality comprising a methyl group, wherein the methyl group is a functional group which is an alkyl group. Similarly, the 2-nitrocyclobut-1-yl group is a $C_4$ cycloaliphatic functionality comprising a nitro group, wherein the nitro group is a functional group. A cycloaliphatic functionality may comprise one or more halogen atoms which may be the same or different. Exemplary cycloaliphatic functionalities comprise cyclopropyl, cyclobutyl, 1,1,4,4-tetramethylcyclobutyl, piperidinyl, 2,2,6,6-tetramethylpiperydinyl, cyclohexyl and cyclopentyl.

As used herein, the term "aromatic functionality" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic functionality" includes but is not limited to, phenyl, pyridyl, furanyl, thienyl, naphthyl, phenylene, and biphenyl functionalities. The aromatic functionality may also include nonaromatic components. For example, a benzyl group is an aromatic functionality that comprises a phenyl ring (the aromatic group) and a methylene group (the nonaromatic component). Similarly a tetrahydronaphthyl functionality is an aromatic functionality comprising an aromatic group ($C_6H_3$) fused to a nonaromatic component ($CH_2)_4$. For convenience, the term "aromatic functionality" is defined herein to encompass a wide range of functional groups such as alkyl groups, haloalkyl groups, haloaromatic groups, alcohol groups, ether groups, carboxylic acid groups, acyl groups (for example carboxylic acid derivatives such as esters and amides), amine groups and nitro groups. For example, the 4-methylphenyl functionality is a $C_7$ aromatic functionality comprising a methyl group, wherein the methyl group is a functional group which is an alkyl group. Similarly, the 2-nitrophenyl group is a $C_6$ aromatic functionality comprising a nitro group, wherein the nitro group is a functional group. Aromatic functionalities include halogenated aromatic functionalities. Exemplary aromatic functionalities include, but are not limited to, phenyl, 4-trifluoromethylphenyl, 4-chloromethylphen-1-yl, 3-trichloromethylphen-1-yl (3-CCl$_3$Ph-), 4-(3-bromoprop-1-yl)phen-1-yl (4-BrCH$_2$CH$_2$CH$_2$Ph-), 4-aminophen-1-yl (4-H$_2$NPh-), 4-hydroxymethylphen-1-yl (4-HOCH$_2$Ph-), 4-methylthiophen-1-yl (4-CH$_3$SPh-), 3-methoxyphen-1-yl and 2-nitromethylphen-1-yl (2-NO$_2$CH$_2$Ph), and naphthyl.

As used herein the term "aliphatic functionality" refers to a linear or branched array of atoms that is not cyclic and has a valence of at least one. Aliphatic functionalities are defined to comprise at least one carbon atom. The array of atoms may include heteroatoms such as nitrogen, sulfur, silicon, selenium and oxygen or may be composed exclusively of carbon and hydrogen. For convenience, the term "aliphatic functionality" is defined herein to encompass, as part of the "linear or branched array of atoms which is not cyclic" a wide range of functional groups such as alkyl groups, haloalkyl groups, alcohol groups, ether groups, carboxylic acid groups, acyl groups (for example carboxylic acid derivatives such as esters and amides), amine groups and nitro groups. For example, the 4-methylpent-1-yl is a $C_6$ aliphatic functionality comprising a methyl group, wherein the methyl group is a functional group which is an alkyl group. Similarly, the 4-nitrobut-1-yl group is a $C_4$ aliphatic functionality comprising a nitro group, wherein the nitro group is a functional group. An aliphatic functionality may be a haloalkyl group which comprises one or more halogen atoms which may be the same or different. Exemplary aliphatic functionalities include, but are not limited to, methyl, ethyl, propyl, isopropyl, butyl, isobutyl, pentyl, isopentyl, trifluoromethyl, bromodifluoromethyl, chlorodifluoromethyl, chloromethyl, trichloromethyl, bromoethyl, 2-hexyl, hexamethylene, hydroxymethyl (i.e., CH$_2$OH), mercaptomethyl (CH$_2$SH), methylthio (SCH$_3$), methylthiomethyl (CH$_2$SCH$_3$), methoxy, methoxycarbonyl (CH$_3$OCO), nitromethyl (CH$_2$NO$_2$) and thiocarbonyl.

Disclosed herein are dihydroxy aromatic compounds having a Formula (I),

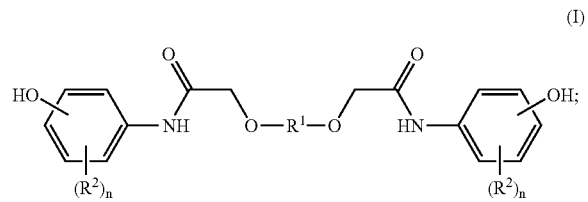

wherein $R^1$, $R^2$ and "n" are defined as above.

In one embodiment the dihydroxy aromatic compound comprises compounds of Formula (X), Formula (XI), Formula (XII) or Formula (XIII),

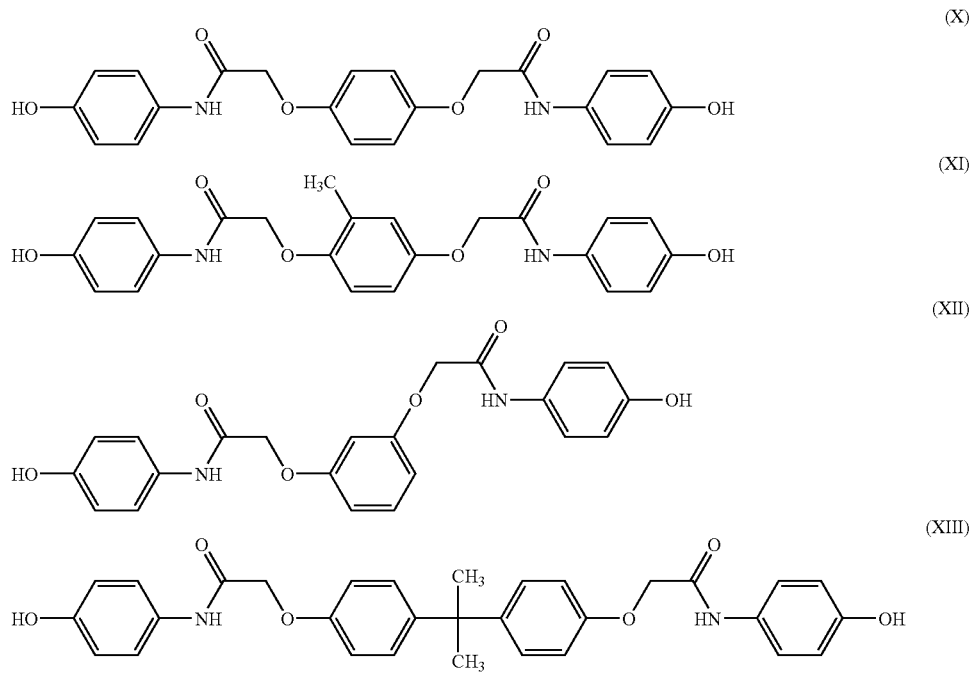

wherein $R^1$ is derived from hydroquinone in Formula (X), from methyl hydroquinone in Formula (XI), from resorcinol in Formula (XII) and from bisphenol A in Formula (XIII), and "n" in Formula (X), Formula (XI), Formula (XII) and Formula (XIII) is 0. The compounds of Formula (X), Formula (XI), Formula (XII) and Formula (XIII) may hereinafter also be referred to as N-(4-hydroxy-phenyl)-2-[4-[(4-hydroxy-phenylcarbomoyl)-methoxy]-phenoxy]-acetamide; N-(4-hydroxy-phenyl)-2-[4-[(4-hydroxy-phenylcarbomoyl)-methoxy]-2-methyl-phenoxy]-acetamide, N-(4-hydroxyphenyl)-2-(3-[(4-hydroxyphenylcarbomoyl)-methoxy]-phenoxy)-acetamide and N-(4-hydroxy-phenyl)-2-(4-(1-methyl-1-[4-(4-hydroxyphenlycarbomyl-methoxy)-phenyl]-ethyl)-phenoxy)-acetamide respectively.

The process for making the dihydroxy compound of Formula (I) comprises the following steps. The first step comprises reacting a compound of Formula (III) with a compound of Formula (IV) in the presence of a first base to produce a compound of Formula (V)

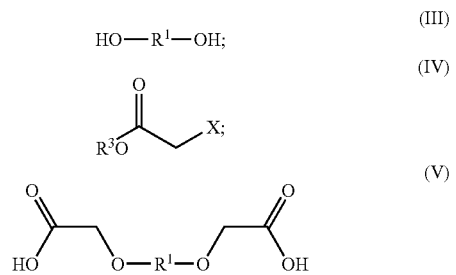

wherein $R^1$, $R^3$ and X have the same meaning as defined above.

Suitable compounds of Formula (III) can be represented by bisphenol compounds having Formula (XIV),

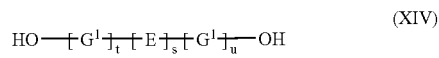

wherein each $G^1$ is independently at each occurrence an aromatic functionality having 6 to 20 carbons; E is independently at each occurrence, a cycloaliphatic functionality having 3 to 20 carbons, an aromatic functionality having 6 to 20 carbons, an aliphatic functionality having 1 to 20 carbons, a sulfur-containing linkage (for example, —S—, —SO—, —SO$_2$—), a selenium-containing linkage (for example, —Se—, —SeO—, —SeO$_2$—), a phosphorus-containing linkage, or an oxygen atom; "t" is a number greater than or equal to one and less than or equal to 10,000; "s" is either zero or one; "u" is a number including zero to 10,000. When "s" equals zero then $[G^1]_t$ is bonded to $[G^1]_u$.

Exemplary compounds having Formula (XIV) include, but are not limited to, 1,1-bis(4-hydroxyphenyl)cyclopentane; 2,2-bis(3-allyl-4-hydroxyphenyl)propane; 2,2-bis(2-t-butyl-4-hydroxy-5-methylphenyl)propane; 2,2-bis(3-t-butyl-4-hydroxy-6-methylphenyl)propane; 2,2-bis(3-t-butyl-4-hydroxy-6-methylphenyl)butane; 1,3-bis[4-hydroxyphenyl-1-(1-methylethylidine)]benzene; 1,4-bis[4-hydroxyphenyl-1-(1-methylethylidine)]benzene; 1,3-bis[3-t-butyl-4-hydroxy-6-methylphenyl-1-(1-methylethylidine)]benzene; 1,4-bis[3-t-butyl-4-hydroxy-6-methylphenyl-1-(1-methylethylidine)]benzene; 4,4'-biphenol; 2,2-bis(3-methyl-4-hydroxyphenyl)propane; 1,1-bis(4-hydroxyphenyl)norbornane; 1,2-bis(4-hydroxyphenyl)ethane; bis(4-hydroxyphenyl)sulfide; 4,4'-oxydiphenol; 2-phenyl-3,3-bis(4-hydroxyphenyl)phthalimidine; 2,4'-dihydroxydiphenylmethane; 2-bis(2-hydroxyphenyl)methane; bis(4-hydroxyphenyl)methane; bis(4-hydroxy-5- nitrophenyl)methane; bis(4-hydroxy-2,6-dimethyl-3-methoxyphenyl)methane; 1,1-bis(4-hydroxyphenyl)ethane; 2,2-bis(4-hydroxyphenyl)propane (bisphenol A); 1,1-bis(4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dimethyl-4-hydroxyphenyl)propane; 2,2-bis(3,5-disopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetramethylphenyl)propane; 2,2-bis(4-hydroxy-3-ethylphenyl)propane; 2,2-bis(4-hydroxy-3,5-dimethylphenyl)propane; 1,1-bis(4-hydroxyphenyl)cyclohexylmethane; 2,2-bis(4-hydroxyphenyl)-1-phenylpropane; 1,1-bis(4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dimethyl-4-hydroxyphenyl)cyclohexane; 4,4'-[1-methyl-4-(1-methyl-ethyl)-1,3-cyclohexandiyl]bisphenol (1,3BHPM); 4-[1-[3-(4-hydroxyphenyl)-4-methylcyclohexyl]-1-methyl-ethyl]-phenol (2,8-BHPM); 1,1-bis(3,5-disopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetramethylphenyl)cyclohexane; 1,1-bis(4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dimethyl-4-hydroxyphenyl)-3,3,5-trimethylcyclohexane; 1,1-bis(3,5-disopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetramethylphenyl)-3,3,5-trimethylcyclohexane; 4,4-bis(4-hydroxyphenyl)heptane; 1,1-bis(4-hydroxyphenyl)decane; 1,1-bis(4-hydroxyphenyl)cyclododecane; 1,1-bis(3,5-dimethyl-4-hydroxyphenyl)cyclododecane; 4,4'dihydroxy-1,1-biphenyl; 4,4'-dihydroxy-3,3'-dimethyl-1,1-biphenyl; 4,4'-dihydroxy-3,3'-dioctyl-1,1-biphenyl; 4,4'-(3,3,5-trimethylcyclohexylidene)diphenol; 4,4'-bis(3,5-dimethyl) diphenol; 4,4'-dihydroxydiphenylether; 4,4'-dihydroxydiphenylthioether; 1,3-bis(2-(4-hydroxyphenyl)-2-propyl)benzene; 1,3-bis(2-(4-hydroxy-3-methylphenyl)-2-propyl)benzene; 1,4-bis(2-(4-hydroxyphenyl)-2-propyl) benzene; 1,4-bis(2-(4-hydroxy-3-methylphenyl)-2-propyl) benzene; 2,4'-dihydroxyphenyl sulfone; 4,4'-dihydroxydiphenylsulfone (BPS); bis(4-hydroxyphenyl) methane; 2,6-dihydroxy naphthalene; hydroquinone; methyl hydroquinone; resorcinol; $C_{1-3}$ alkyl-substituted resorcinols; 3-(4-hydroxyphenyl)-1,1,3-trimethylindan-5-ol; 1-(4-hydroxyphenyl)-1,3,3-trimethylindan-5-ol; 4,4-dihydroxydiphenyl ether; 4,4-dihydroxy-2,5-dihydroxydiphenyl ether; 4,4-thiodiphenol; 2,2,2',2'-tetrahydro-3,3,3',3'-tetramethyl-1,1'-spirobi[1H-indene]-6,6'-diol; and combinations of two or more of the foregoing.

The amount of the compound of Formula (IV) employed in the reaction can be about 1 mole to about 6 moles per mole of compound of Formula (III) employed. Within this range the amount may be greater than or equal to about 1.5 moles, or, more specifically, greater than or equal to about 2 moles. Also within this range the amount may be less than or equal to about 4 moles, or, more specifically, less than or equal to about 2.5 moles.

One exemplary first base comprises alkali metal hydroxide or alkaline earth metal hydroxide. Another exemplary first base comprises alkali metal carbonate or alkaline earth metal carbonate in combination with alkali metal halide or alkaline earth metal halide.

Specific examples of suitable alkali metal hydroxides or alkaline earth metal hydroxides that can be employed as the first base include, but are not limited to, sodium hydroxide, potassium hydroxide, lithium hydroxide, rubidium hydroxide, cesium hydroxide, calcium hydroxide, magnesium hydroxide and combinations of two or more of the foregoing hydroxides. In one embodiment the first base comprises sodium hydroxide. The alkali metal hydroxides or alkaline earth metal hydroxides can be added as an aqueous solution or as a solid. The amount of first base employed when the first base is an alkali metal hydroxide or an alkaline earth metal hydroxide can be about 1 mole to about 10 moles per mole of the compound of Formula (III) employed. Within this range the amount may be greater than or equal to about 1.5 moles, or, more specifically, greater than or equal to about 2 moles. Also within this range the amount may be less than or equal to about 5 moles, or, more specifically, less than or equal to about 3 moles.

Suitable alkali metal carbonates or alkaline earth metal carbonates that can be used in combination with alkali metal halides or alkaline earth metal halides include, but are not limited to, potassium carbonate, sodium carbonate, calcium carbonate and magnesium carbonate, and combinations of two or more of the foregoing carbonates. The amount of alkali metal carbonate or alkaline earth metal carbonate used in the reaction can be about 1 mole to about 5 moles per mole of the compound of Formula (III) employed. Within this range the amount may be greater than or equal to about 2 moles, or, more specifically, greater than or equal to about 2.5 moles. Also within this range the amount may be less than or equal to about 4 moles, or, more specifically, less than or equal to about 3 moles.

Suitable alkali metal halides or alkaline earth metal halides that can be used in combination with alkali metal carbonate or alkaline earth metal carbonate include, but are not limited to, sodium iodide, potassium iodide and a combination of sodium iodide and potassium iodide. The amount of alkali metal halide or alkali earth metal halide employed in the reaction can be about 1 mole to about 5 moles per mole of the compound of Formula (III) employed. Within this range the amount may be greater than or equal to about 2 moles, or, more specifically, greater than or equal to about 2.5 moles. Also within this range the amount may be less than or equal to about 4 moles, or, more specifically, less than or equal to about 3 moles.

In one embodiment the alkali metal carbonate is potassium carbonate and the alkali metal halide is sodium iodide. The amount of alkali metal carbonate or alkaline earth metal carbonate can be about 1 mole to about 3 moles per mole of alkali metal halide or alkali earth metal halide. Within this range the amount may be greater than or equal to about 1.5 moles, or, more specifically, greater than or equal to about 2 moles. Also within this range the amount may be less than or equal to about 2.75 moles, or, more specifically, less than or equal to about 2.5 moles.

Specific examples of solvents that can be employed in the reaction of the compound of Formula (III) with the compound of Formula (IV) include, but are not limited to, water, acetone, dimethylformamide (DMF), tetrahydrofuran (THF), diphenylether, dimethylsulfoxide (DMSO) and combinations of two or more of the foregoing solvents. In one embodiment the solvent employed comprises water, acetone or a combination of water and acetone. In certain embodiments the amount of solvent employed in the reaction of the compound of Formula (III) with the compound of Formula (IV) can be about 1 liter to about 10 liters per mole of compound of Formula (III). Within this range the amount may be greater than or equal to about 3 liters, or, more specifically, greater than or equal to about 5 liters. Also within this range the amount may be less than or equal to about 8 liters, or, more specifically, less than or equal to about 6 liters.

The temperature at which the reaction of the compound of Formula (III) with the compound of Formula (IV) proceeds can be about 30° C. to about 100° C. Within this range the temperature may be greater than or equal to about 40° C., or, more specifically, greater than or equal to about 60° C. Also within this range the temperature may be less than or equal to about 90° C., or, more specifically, less than or equal to about 80° C. The time taken for the reaction of the compound of Formula (III) with the compound of Formula (IV) can be about 5 hours to about 50 hours. Within this range the time may be greater than or equal to about 10 hours, or, more specifically, greater than or equal to about 20 hours. Also within this range the time may be less than or equal to about 45 hours, or, more specifically, less than or equal to about 40 hours.

The reaction of the compound of Formula (III) with the compound of Formula (IV) directly provides the compound of Formula (V) when $R^3$ is H. When $R^3$ is an aliphatic functionality the reaction of a compound of Formula (III) with the compound of Formula (IV) under the conditions described above provides a diester having the formula

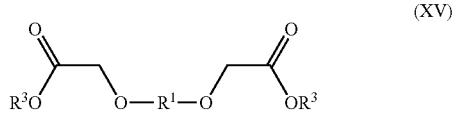

(XV)

wherein $R^1$ is as described above.

The diester of Formula (XV) can be hydrolyzed in the presence of an alkali metal hydroxide or alkali metal carbonate to provide the corresponding diacid compound of Formula (V). Exemplary alkali metal hydroxide or alkali metal carbonates include but are not limited to, sodium hydroxide, potassium hydroxide, lithium hydroxide, cesium hydroxide, sodium carbonate, potassium carbonate and combinations of two or more of the foregoing hydroxides.

The amount of alkali metal hydroxide or alkali metal carbonate employed in the hydrolysis can be about 1 mole to about 8 moles per mole of diester of Formula (XV). Within this range the amount may be greater than or equal to about 2 moles, or, more specifically, greater than or equal to about 3 moles. Also within this range the amount may be less than or equal to about 6 moles, or, more specifically, less than or equal to about 5 moles.

Suitable solvent that can be used in the hydrolysis reaction of the diester of Formula (XV) to the corresponding diacid of Formula (V) includes but is not limited to, ethanol, methanol, tetrahydrofuran and dioxane. The amount of solvent employed in the hydrolysis reaction can be about 0.5 liters to about 4 liters per mole of diester of Formula (XV). Within this range the amount may be greater than or equal to about 1 liter, or, more specifically, greater than or equal to about 1.5 liters. Also within this range the amount may be less than or equal to about 3 liters, or, more specifically, less than or equal to about 2.5 liters.

The temperature of the hydrolysis reaction of the compound of Formula (XV) can be about 25° C. to about 80° C. Within this range the temperature may be greater than or equal to about 30° C., or, more specifically, greater than or equal to about 40° C. Also within this range the temperature may be less than or equal to about 70° C., or, more specifically, less than or equal to about 60° C. The time taken for the hydrolysis reaction can be about 10 hours to about 24 hours. Within this range the time may be greater than or equal to about 12 hours, or, more specifically, greater than or equal to about 16 hours. Also within this range the time may be less than or equal to about 20 hours, or, more specifically, less than or equal to about 18 hours.

The compound of Formula (V) is reacted in the presence of a first catalyst with a halogenating agent to provide the corresponding diacid halide having Formula (VI)

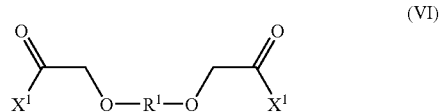

(VI)

wherein $R^1$ and $X^1$ are as described above.

Exemplary halogenating agents include, but are not limited to, thionyl chloride, phosphorous trichloride, phosphorous pentachloride, phosphorous pentabromide, thionyl bromide, phosphorous tribromide, and oxalyl chloride. In one embodiment the halogenating agent is thionyl chloride.

The amount of halogenating agent employed in the reaction can be about 2 moles to about 10 moles per mole of compound of Formula (V). Within this range the amount may be greater than or equal to about 2.5 moles, or, more specifically, greater than or equal to about 3 moles. Also within this range the amount may be less than or equal to about 8 moles, or, more specifically, less than or equal to about 4 moles.

Suitable first catalysts that can be employed in the halogenation of the compound of Formula (V) or include, but are not limited to, dimethylformamide, dimethylacetamide, dimethylaminopyridine, dimethylaniline, diethylamine and combinations of two or more of the foregoing catalysts.

The amount of first catalyst employed in the reaction can be 0.01 moles to about 0.1 moles per mole of compound of Formula (V). Within this range the amount may be greater than or equal to about 0.02 moles, or, more specifically, greater than or equal to about 0.03 moles. Also within this range the amount may be less than or equal to about 0.08 moles, or, more specifically, less than or equal to about 0.05 moles.

Suitable solvents that can be employed in the halogenation of the compound of Formula (V) include, but are not limited to, toluene, xylene, chloroform, methylene dichloride, ethylene dichloride and carbon tetrachloride. In one embodiment the solvent used is ethylene dichloride.

In certain embodiments the amount of solvent employed in the halogenation of the compound of Formula (V) can be about 1.5 liters to about 3.0 liters per mole of compound of Formula (V). Within this range the amount may be greater than or equal to about 1.75 liters, or, more specifically, greater than or equal to about 2.0 liters. Also within this range the amount may be less than or equal to about 2.75 liters, or, more specifically, less than or equal to about 2.25 liters.

The temperature of the halogenation reaction of the compound of Formula (V) (can be about 40° C. to about 140° C. Within this range the temperature may be greater than or equal to about 60° C., or, more specifically, greater than or equal to about 80° C. Also within this range the temperature may be less than or equal to about 120° C., or, more specifically, less than or equal to about 90° C. The time taken for the halogenation reaction of the compound of Formula (V) can be about 1 hour to about 10 hours. Within this range the time may be greater than or equal to about 3 hours, or, more specifically, greater than or equal to about 4 hours. Also within this range the time may be less than or equal to about 8 hours, or, more specifically, less than or equal to about 6 hours.

The compound of Formula (VI) is reacted with a compound of Formula (VII) in the presence of a second base to produce a compound of Formula (I)

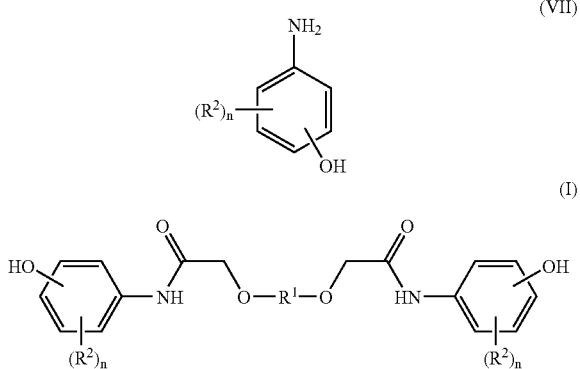

wherein $R^1$, $R^2$ and "n" have the same meaning as defined above.

Suitable compounds having Formula (VII) include, but are not limited to, 4-aminophenol, 3-aminophenol, 2-methyl-4-aminophenol, 4-chloro-2-aminophenol, 2-amino-4-chlorophenol, 2-amino-5-chlorophenol and 4-amino-2-nitrophenol. In one embodiment the compound of Formula (VII) comprises 4-aminophenol having Formula (IX) shown below.

The amount of the compound of Formula (VII) employed in the reaction can be 1 mole to about 5 moles per mole of compound having Formula (VI). Within this range the amount may be greater than or equal to about 2 moles, or, more specifically, greater than or equal to about 2.5 moles. Also within this range the amount may be less than or equal to about 4 moles, or, more specifically, less than or equal to about 3 moles.

Suitable second bases include, but are not limited to, organic or inorganic bases having sufficient strength to remove a proton from the amine group of the compound of Formula (VII) without removing substantial amounts of protons from the hydroxy group. Specific examples of inorganic bases include alkali metal hydroxides or alkaline earth metal hydroxides including, but not limited to, sodium hydroxide, potassium hydroxide, lithium hydroxide, rubidium hydroxide cesium hydroxide, calcium hydroxide, magnesium hydroxide and combinations of two or more of the foregoing alkali metal hydroxides. In one embodiment the second base comprises sodium hydroxide. Specific examples of organic bases include but are not limited to, triethylamine, piperidine, piperidine, ethyldiisopropylamine, triethylamine, pyridine, pyrrolidone, morpholine, sodium carbonate, potassium carbonate, sodium methylate, potassium methylate and combinations of two or more of the foregoing. The second base can be added as an aqueous solution or as a solid.

The amount of second base employed in the reaction can be about 0.5 moles to about 3 moles per mole of compound of Formula (VII) employed. Within this range the amount may be greater than or equal to 1 mole, or, more specifically, greater than or equal to about 1.5 moles. Also within this range the amount may be less than or equal to about 2.5 moles, or, more specifically, less than or equal to about 2 moles.

Specific examples of suitable solvents that can be employed in the reaction of the compound of Formula (VI) in the presence of a second base with a compound of Formula (VII) include, but are not limited to, dimethylformamide, dimethylsulfoxide, dimethylacetamide, tetrahydrofuran, dioxane, ethylene dichloride, methylene dichloride, chloroform, carbon tetrachloride and combinations of two or more of the foregoing. In one embodiment the solvent employed comprises dimethylformamide, dimethylacetamide, or a combination of the two. The amount of solvent employed in the reaction of compound having the compound of Formula (VI) in the presence of a second base with a compound of Formula (VII) can be about 0.5 liters to about 3 liters per mole of having the compound of Formula (VII). Within this range the amount may be greater than or equal to 1 liter, or, more specifically, greater than or equal to about 1.5 liters. Also within this range the amount may be less than or equal to about 2.5 liters, or, more specifically, less than or equal to about 2 liters.

The temperature of the reaction of a compound of Formula (VI) in the presence of a second base with a compound of Formula (VI) can be about 0° C. to about 40° C. Within this range the temperature may be greater than or equal to about 5° C., or, more specifically, greater than or equal to about 10° C. Also within this range the temperature may be less than or equal to about 30° C., or, more specifically, less than or equal to about 25° C. The time for the reaction of compound of Formula (VI) in the presence of a second base with a compound of Formula (VII) can be about 5 hours to about 40 hours. Within this range the time may be greater than or equal to about 10 or, more specifically, greater than or equal to about 20 hours. Also within this range the time may be less than or equal to about 35 hours, or, more specifically, less than or equal to about 30 hours.

In one embodiment a process for producing the dihydroxy aromatic compounds of Formula (II) comprises reacting a compound of Formula (III) with a compound of Formula (IV) in the presence of a first base to produce a compound of Formula (V)

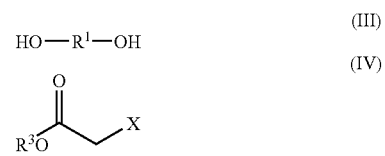

-continued

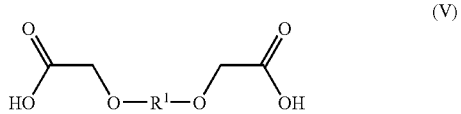
(V)

reacting the compound of Formula (V) in the presence of a first catalyst with a chlorinating agent to provide the corresponding diacid chloride having Formula (VIII)

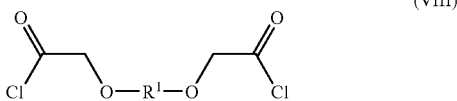
(VIII)

and reacting the compound of Formula (VIII) in the presence of a second base with 4-aminophenol (Formula (IX)) to produce a compound of Formula (II)

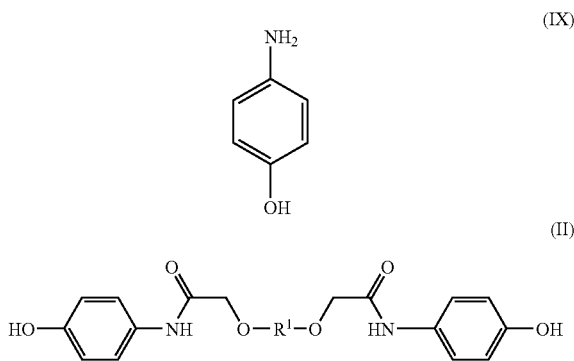

wherein $R^1$ is derived from hydroquinone, methyl hydroquinone, resorcinol or bisphenol A, $R^3$ is hydrogen or methyl and "n" is an integer having a value 0 to 4.

In one embodiment a composition comprises a compound of Formula (I)

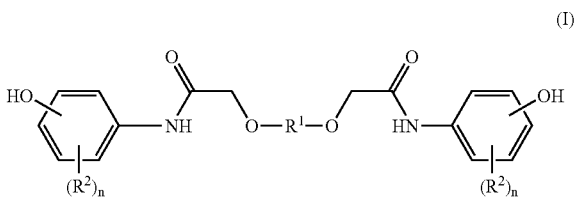
(I)

wherein $R^1$, $R^2$, and "n" are defined as above.

As previously discussed, one of the end uses of the compounds of Formula (I) is use in the preparation of polymers for example, polycarbonates, polyesters, polyurethanes, and epoxide containing polymers. Suitable methods for preparation of polycarbonates include, but are not limited to, interfacial polymerization where compounds of Formula (I) react with phosgene, and melt-transesterification reactions of the compound of Formula (I) and possibly other bisphenols with e.g. diphenylcarbonate in the presence of quaternary phosphonium salts, tetraalkylammonium salts, and/or sodium hydroxide as catalyst systems.

A further understanding of the techniques described above can be obtained by reference to certain specific examples that are provided herein for purposes of illustration only, and are not intended to be limiting.

EXAMPLES

High Performance Liquid Chromatography (HPLC) was used to identity the conversion of product compound. An Xterra C18 column, length 15 centimeters, inner diameter 4.6 millimeters and thickness 5 micrometers was used for the analysis. The column temperature was maintained at 30° C. The column was eluted with 90% of water (containing 0.05% of orthophosphoric acid) and 10% acetonitrile. The flow rate of sample in the column was maintained at 1.00 ml/min and amount of sample injected was 5 microliter. The total run time was 35 min.

Proton NMR spectra for the starting materials and products described herein were measured using a 300 megahertz Bruker NMR spectrometer using deuterated chloroform or $d_6$-dimethylsulfoxide as a solvent. Compounds were further characterized by a liquid chromatograph-mass spectrometer (LC-MS) system, comprising a liquid chromatograph and a Quattro Ultima Pt mass spectrometer.

Example 1

This example provides a method for the preparation of N-(4-Hydroxy-phenyl)-2-[4-[(4-hydroxy-phenylcarbamoyl)-methoxy]-phenoxy]-acetamide. The method includes 3 steps as described below.

Step A: Preparation of (4-carboxymethoxy-phenoxy)-acetic Acid (diacid)

To an aqueous solution of sodium hydroxide (88 grams (g) in 267 milliliters (ml) of water) was charged 1,4-hydroquinone (55 g; purity greater than 99%) portion-wise and the resultant mixture was stirred under nitrogen atmosphere. The mixture was cooled to 10° C. and an aqueous solution of chloroacetic acid (CAA, 94.5 g in 47.2 ml of water) was added dropwise to the hydroquinone solution prepared above, maintaining the temperature of the resultant reaction mixture below 10° C. The reaction mixture was stirred for about 30 minutes (min) at 10° C. The reaction mixture was then heated to 80° C. and maintained at 80° C. for about 36 hours (hrs) to about 48 hrs, under $N_2$ atmosphere. The reaction was monitored by HPLC after about 6 hrs after heating to 80° C. An aqueous solution of chloroacetic acid (9.4 g dissolved in 19.8 ml water) was added since the presence of monoacid was detected in the reaction mixture. Heating was continued at 80° C. for an additional 1 to 3 hrs and the procedure repeated until the concentration of monoacid was less than 3% (based on LC/NMR). The reaction mixture was cooled to 25° C. and the contents acidified by adding aqueous HCl (1:1; 0–5° C.) with stirring. The solid was collected by filtration and washed with water until the washings were neutral. The solid was dried at 85° C. in an oven for about 8 hrs. The product weighed 45 g and had a purity of 90 percent as determined by HPLC.

Purification of (4-carboxymethoxy-phenoxy)-acetic Acid (diacid):

The diacid prepared above (30 g) was dissolved in 90 ml of dimethylformamide and warmed to 60° C. and charcoal (0.5 g) was added. The hot mixture was filtered through a celite bed. The filtrate was diluted with 90 ml of methanol and 600 ml of demineralized water under stirring to precipitate the solid. The resulting solid was filtered and dried. The product obtained after purification weighed 32 g at 99 percent purity. The NMR peaks for the product were $^1$H NMR: DMSO-d$_6$: δ 4.6 (m, 4H, O—CH$_2$), 6.85 (m, 4H, Ar—O—H). (DMSO-dimethylsulfoxide)

Step B: Preparation of Diacid Chloride of (4-carboxymethoxy-phenoxy)-acetic Acid The purified diacid from Step A (40.25 g, dry product) was charged to a reaction flask. 1,2-dichloroethane (125 ml) and dimethylformamide (5 ml) were then added to the diacid. Thionyl chloride (47.2 g) was added dropwise to the diacid-dichloroethane mixture. After completion of the addition of thionyl chloride, the resultant mixture was heated at 85° C. and maintained for about 6 hrs. Then the mixture was cooled to room temperature (25° C.). The excess thionyl chloride and 1,2-dichloroethane were distilled off at 55 to 60° C. under vacuum. After complete removal of solvents and excess thionyl chloride, 1,2-dichloroethane (25 ml) was charged to the residue and distilled off to get the diacid chloride solids.

Step C: N-(4-hydroxy-phenyl)-2-[4-[(4-hydroxy-phenylcarbamoyl)-methoxy]-phenoxy]-acetamide.

The diacid chloride obtained from Step B, was dissolved in dimethylformamide (100 ml) and stored under N$_2$ atmosphere. A solution of 4-amino phenol (26.2 g dissolved in 125 ml dimethylformamide) was put under a N$_2$ atmosphere. The mixture was stirred to get a clear solution and then triethylamine (25 g) was added. The mixture was cooled to about 0 to 5° C. and then stirred for about 30 min. The diacid chloride solution prepared above was charged in a dropping funnel and added over a period of 30 minutes to the stirred solution of aminophenol-triethylamine kept at about 0 to 5° C. The mixture was then stirred for about 1 hr at 5° C. and stirred at room temperature for about 2 hrs. The reaction was monitored by HPLC to check for the disappearance of 4-aminophenol. When the aminophenol content was below 2%, the mixture was acidified with HCl (12 ml, 1:1, 0 to 5° C.). The resultant mixture was stirred for 30 min and then the solid was filtered under suction. The solid was washed with water until the washings were neutral. The material was dried in an oven at 65 to 70° C. for about 6 hrs. The product obtained weighed 45 g and showed 90 to 92 percent purity based on HPLC.

Purification of the Final Product

The product obtained in step C (50 g) was dissolved in 200 ml of dimethylformamide and heated to obtain a clear solution (70° C.). An aqueous solution of sodium bisulphate (0.5 g in 1 ml of water) was added to the dimethylformamide solution and stirred for 20 min. Charcoal (2 g) was added to the mixture and heated for 5 min. The resulting slurry was filtered. Water (200 ml) was added to the filtrate under stirring. The resulting solid was filtered and the material air dried under vacuum for about 2 hrs. The solids were suspended in 300 ml of acetonitrile and heated to about 65° C. The slurry was then filtered. The solid was dried and purity checked by HPLC. The solid was dried in an oven at 85° C. for about 6 hrs. The product obtained weighed 36 g with purity of 99.2% based on LC. NMR data: $^1$H NMR: DMSO-d$_6$: δ 4.52 (m, 4H, O—CH2), 6.7 (m, 4H, Ar—O—H), 6.9 (m, 4H, Ar—NH—H), 7.4 (m, 4H, quinol-H), 9.3 (bs, 2H, OH), 9.7 (bs, 2H, NH)

Example 2

This example provides a method for the preparation of N-(4-hydroxy-phenyl)-2-[4-[(4-hydroxy-phenylcarbamoyl)-methoxy]-phenoxy]-acetamide. The method includes 3 steps as described below.

Step A: Preparation of (4-carboxymethoxy-2-methyl-phenoxy)-acetic Acid (diacid)

(4-carboxymethoxy-2-methyl-phenoxy)-acetic acid was prepared using the same procedure described for Step A in Example 1 except that hydroquinone was substituted with methyl hydroquinone (62 g). Other reagents and solvents were used as described in the procedure mentioned above. The product obtained weighed 50 g with a purity of 95 percent as indicated by HPLC.

Purification of the (4-carboxymethoxy-2-methyl-phenoxy)-acetic Acid (diacid).

A solution of diacid (30 g in 90 ml of dimethylformamide) was warmed to about 60° C. and charcoal (0.5 g) was added. The slurry was filtered through celite bed and the filtrate diluted with methanol (90 ml) and demineralized water (600 ml) under stirring. The resulting solid was filtered and dried. The product obtained after purification weighed 36 g with a purity of 99 percent as indicated by LC. NMR data: $^1$H NMR: DMSO-d$_6$: δ 2.18 (m, 3H), 4.6 (m, 4H, O—CH$_2$), 6.6–6.8 (m, 4H, Ar—O—H).

Step B: Preparation of (4-chlorocarbonylmethoxy-2-methyl-phenoxy)-acetyl chloride (diacid chloride)

The diacid chloride was prepared using the same procedure as used in Step B of Example 1 except that (4-carboxymethoxy-2-methyl-phenoxy)-acetic acid of Example 2 was used in place of (4-carboxymethoxy-phenoxy)-acetic acid of Example 1.

Step C: Preparation of N-(4-hydroxy-phenyl)-2-{4-[(4-hydroxy-phenylcarbamoyl)-methoxy]-phenoxy}-acetamide The acetamide was prepared in a similar manner as in STEP C of Example 1, except in that the diacid chloride of (4-carboxymethoxy-2-methyl-phenoxy)-acetic acid of Example 2 was used in place of (4-carboxymethoxy-phenoxy)-acetic acid of Example 1. The product obtained weighed 45 g with a purity of 90 to 92 percent as indicated by LC/MS. NMR Data: $^1$H NMR: DMSO-d$_6$: δ 2.3 (s, 3H, Me-H), 4.6 (m, 4H, Ar—O—CH2), 6.6 (m, 7H, Ar—O—H and quinol-H), 7.4 (m, 4H, Ar—NH—H), 9.3 (bs, 2H, OH), 9.7 (bs, 2H, NH).

Example 3

This example provides a method for the preparation of N-(4-hydroxy-phenyl)-2-(4-(1-methyl-1-[4-(4-hydroxyphenlycarbomyl-methoxy)-phenyl]-ethyl)-phenoxy)-acetamide. The method involves 3 steps as described below.

Step A: Preparation of (4-[1-(4-ethoxycarbonylmethoxy-phenyl)-1-methyl-ethyl]-phenoxy)-acetic Acid ethyl ester (diester)

Potassium carbonate (41.4 g) was added to solution of BPA in acetone (22.8 g in 310 ml acetone) at room temperature. Sodium iodide (45.0 g) was charged to the above mixture. Ethylbromo acetate (52.0 g) was added drop-wise to the above mixture at room temperature. The resultant mixture was then refluxed at 65° C. (bath temperature; reaction temperature at 55° C.) for about 36 hrs. Acetone was distilled off under vacuum at 50° C. under 100 mm Hg. Water (400 ml) was added to the residue and the resultant mixture was extracted with dichloromethane (2×300 ml; 1×100 ml). The organic layer was washed with aqueous sodium hydroxide solution (5 percent solution; 5×200 ml) followed by washing with water (2×300 ml) until the washes indicated a neutral pH. The organic phase was dried over anhydrous sodium sulfate. The dichloromethane was then removed at 50° C. under reduced pressure (400 mm Hg). The product obtained was an oily material weighing 34.7 g.

Step B Preparation (4-[1-(4-carboxymethoxy-phenyl)-1-methyl-ethyl]-phenoxy)-acetic Acid (diacid)

A solution of diester (34.7 g; obtained in Step A) in tetrahydrofuran (290 ml) and ethanol (290 ml) was taken in a reaction vessel. An ethanolic solution of KOH (19.7 g dissolved in 290 ml ethanol) was added to the above solution at room temperature. The resultant milky solution was stirred for about 19 hours at room temperature and the solvent was removed under reduced pressure (60° C. at 10 mm Hg). The solid obtained was dissolved in water (400 ml) and washed with ether (150 ml). The aqueous layer was cooled to 10° C. and dilute HCl (4.5 percent, 100 ml) was added to bring the pH of the aqueous layer to about 4 to 5. The resulting mixture was stirred in an ice bath (0 to 5° C.) for 1 hr. The resulting solid was filtered and washed with chilled water (250 ml) until the washings indicated neutral pH. The crude diacid was recrystallized in methanol and dried to get 18.2 g of product.

Preparation of Acid Chloride

A mixture of (4-[1-(4-carboxymethoxy-phenyl)-1-methyl-ethyl]-phenoxy)-acetic acid (diacid; 18.2 g) and dicholoroethane (80 ml) was stirred at room temperature. Thionyl chloride (23 ml) was added drop-wise to the above mixture followed by the addition of dimethylformamide (2 drops) at room temperature. The resultant mixture was refluxed at 90° C. for 4 hours. The solvent was removed at reduced pressure below 60° C. Dicholoroethane (30 ml) was added and then distilled off to remove traces of thionyl chloride. The product obtained was an oily substance with a weight of 20.2 g.

Step C: Preparation of N-(4-hydroxy-phenyl)-2-[4-[1-[4-[(4-hydroxy-phenylcarbamoyl)-methoxy]-phenyl]-1-methyl-ethyl]-phenoxy]-acetamide.

Dimethylformamide (50 ml.), p-amino phenol (13.0 g), and triethylamine (25 ml) were charged to a 250 ml round bottom flask at room temperature. The contents of the flask were cooled to 2 to 5° C. and a solution of the acid chloride prepared in Step B (20.2 g acid chloride dissolved in 35 ml dimethylformamide) was added drop wise over a period of about 30 minutes. The resultant reaction mixture was stirred at 10° C. for about 1 hr and at room temperature for about 20 hours. The reaction mixture was then cooled to 2 to 5° C. and poured on 700 g ice. The resultant mixture was acidified with dilute HCl (10 percent; 10 ml). The solid was then filtered to give a product weighting 85 g (wet weight). The wet product was directly taken for purification.

Purification of N-(4-hydroxy-phenyl)-2-[4-[1-[4-[(4-hydroxy-phenylcarbamoyl)-methoxy]-phenyl]-1-methyl-ethyl]-phenoxy]-acetamide.

The crude solid was dissolved in 400 ml of a 10 percent sodium hydroxide solution and stirred at room temperature for about 30 minutes. The resultant mixture was acidified with dilute HCl (18 percent, 250 ml) and extracted with ethyl acetate. The solution was filtered through cotton to remove any sticky material. The solvent was distilled off and hexane (100 ml) was added to the residue and the resultant mixture stirred for about 20 minutes. The obtained solid was filtered and recrystallized twice with methanol/water (6 parts methanol:1 part water) to get a product weighing 8 g and having a melting point 206° C.

As can be seen from the foregoing examples a compound having Formula (I) can be readily prepared as shown in Examples 1, 2 and 3.

While the invention has been described with reference to an exemplary embodiment, it will be understood by those skilled in the art that various changes may be made and equivalents may be substituted for elements thereof without departing from the scope of the invention. In addition, many modifications may be made to adapt a situation or material to the teachings of the invention without departing from the essential scope thereof. Therefore, it is intended that the invention not be limited to, the embodiment disclosed as the best mode contemplated for carrying out this invention, but that the invention will include all embodiments falling within the scope of the appended claims.

The invention claimed is:

1. A dihydroxy aromatic compound having a Formula (I),

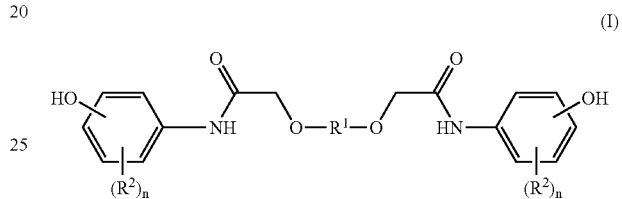

wherein $R^1$ is an aromatic divalent functionality having 6 to 60 carbons, $R^2$ can be the same or different at each occurrence and is independently at each occurrence selected from the group consisting of a cyano functionality, a nitro functionality, a halogen, an aliphatic functionality having 1 to 10 carbons, a cycloaliphatic functionality having 3 to 10 carbons and an aromatic functionality having 6 to 10 carbons, and "n" is an integer having a value of 0 to 4.

2. The dihydroxy aromatic compound of claim 1 wherein the aromatic divalent functionality $R^1$ is derived from a dihydroxy aromatic compound having Formula (XIV)

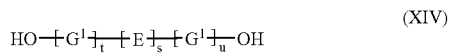

wherein each $G^1$ is independently at each occurrence an aromatic radical having 6 to 20 carbons; E is independently at each occurrence a cycloaliphatic radical having 3 to 20 carbons, an aromatic radical having 6 to 20 carbons, an aliphatic radical having 1 to 20 carbons, a sulfur-containing linkage, a phosphorus-containing linkage, or an oxygen atom; "t" is a number greater than or equal to one and less than or equal to 10,000; "s" is either zero or one; and "u" is a whole number from zero to 10,000.

3. The dihydroxy aromatic compound of claim 1 wherein $R^1$ is derived from hydroquinone, methyl hydroquinone, resorcinol or bisphenol A and "n" equals 0.

4. The dihydroxy aromatic compound of claim 1, wherein the compound of Formula (I) is N-(4-hydroxy-phenyl)-2-[4-[(4-hydroxy-phenylcarbomoyl)-methoxy]-phenoxy]-acetamide.

5. The dihydroxy aromatic compound of claim 1, wherein the compound of Formula (I) is N-(4-hydroxy-phenyl)-2-[4-[(4-hydroxy-phenylcarbomoyl)-methoxy]-2-methyl-phenoxy]-acetamide.

6. The dihydroxy aromatic compound of claim 1, wherein the compound of Formula (I) is N-(4-hydroxy-phenyl)-2-

(4-(1-methyl-1-[4-(4-hydroxyphenlycarbomyl-methoxy)-phenyl]-ethyl)-phenoxy)-acetamide.

7. The dihydroxy aromatic compound of claim 1, wherein the compound of Formula (I) is N-(4-hydroxyphenyl)-2-(3-[(4-hydroxyphenylcarbomoyl)-methoxy]-phenoxy)-acetamide.

8. A process comprising:
reacting a compound of Formula (III) with a compound of Formula (IV) in the presence of a first base to produce a compound of Formula (V)

HO—R¹—OH (III)

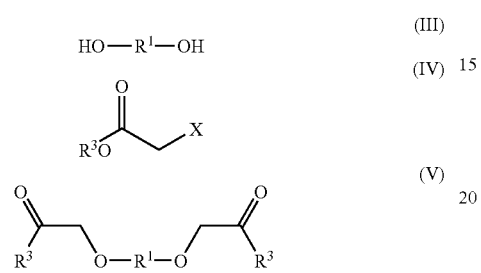

(IV)

(V)

reacting the compound of Formula (V) with a halogenating agent in the presence of a first catalyst to produce a compound of Formula (VI)

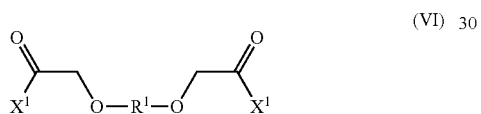

(VI)

and reacting the compound of Formula (VI) with a compound of Formula (VII) in the presence of a second base to produce a compound of Formula (I)

(VII)

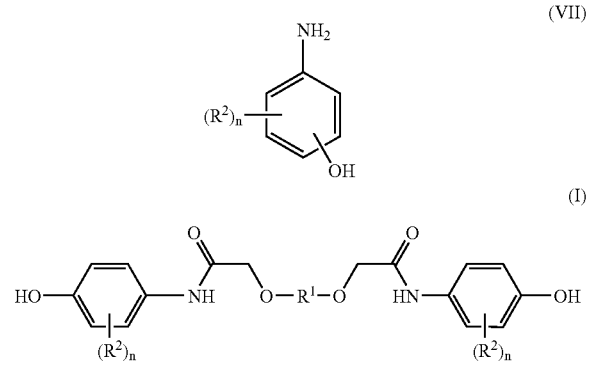

(I)

wherein $R^1$ is an aromatic divalent functionality having 6 to 20 carbons, $R^2$ can be the same or different at each occurrence and is independently at each occurrence selected from the group consisting of a cyano functionality, a nitro functionality, a halogen, an aliphatic functionality having 1 to 10 carbons, a cycloaliphatic functionality having 3 to 10 carbons and an aromatic functionality having 6 to 10 carbons, $R^3$ is a hydrogen or an aliphatic functionality having 1 to 10 carbons, X and $X^1$ are both independently a halogen selected from the group consisting of chlorine and bromine, and "n" is an integer having a value 0 to 4.

9. The process of claim 8, further comprising hydrolyzing the compound of Formula (XIV) in the presence of alkali metal hydroxide or alkali metal carbonate

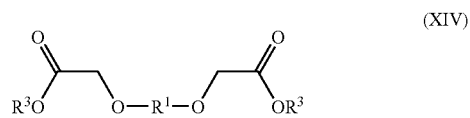

(XIV)

to provide a compound of Formula (V)

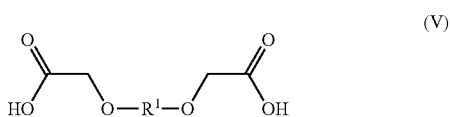

(V)

wherein $R^1$ is an aromatic functionality having 6 to 60 carbons, and $R^3$ is selected from the group consisting of an aliphatic functionality having 1 to 10 carbons.

10. The process of claim 8 wherein the compound of Formula (III) is hydroquinone, methyl hydroquinone, resorcinol or bisphenol A.

11. The process of claim 8 wherein the compound of Formula (IV) comprises chloroacetic acid or ethyl bromo acetate.

12. The process of claim 8 wherein the compound of Formula (VII) is 4-aminophenol.

13. The process of claim 8 wherein the first base is sodium hydroxide.

14. The process of claim 8 wherein the first catalyst is dimethylformamide, dimethylacetamide, dimethylaminopyridine, dimethylaniline or diethylamine.

15. The process of claim 8 wherein the halogenating agent is thionyl chloride, phosphorous trichloride, phosphorous pentachloride, phosphorous pentabromide, thionyl bromide, phosphorous tribromide, or oxalyl chloride.

16. The process of claim 8, wherein the second base is an inorganic base or an organic base.

17. The process of claim 16, wherein the inorganic base is an alkali metal hydroxide or an alkaline earth metal hydroxide.

18. The process of claim 16, wherein the organic base comprises triethylamine, piperidine, piperidine, ethyldiisopropylamine, pyridine, pyrrolidone, morpholine, sodium carbonate, potassium carbonate, sodium methylate, potassium methylate or a combination of two or more of the foregoing.

19. The process of claim 8, wherein the reaction of a compound of Formula (III) with a compound of Formula (IV) occurs at a temperature of about 30° C. to about 100° C.

20. The process of claim 8, wherein the reaction of the compound of Formula (V) with a halogenating agent occurs at a temperature of about 40° C. to about 140° C.

21. The process of claim 8, wherein the reaction of a compound of Formula (VI) with a compound of Formula (VII) occurs at a temperature of about 0° C. to about 40° C.

22. A process comprising;
reacting a compound of Formula (III) with a compound of Formula (IV) in the presence of a first base to produce a compound of Formula (V)

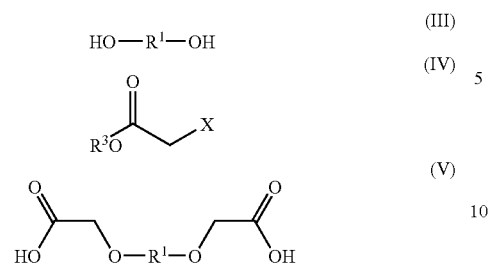

(III)

(IV)

(V)

reacting the compound of Formula (V) in the presence of a first catalyst with a chlorinating agent to provide the corresponding diacid chloride having Formula (VIII)

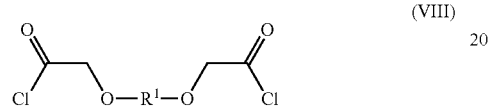

(VIII)

and reacting the compound of Formula (VIII) in the presence of a second base with 4-aminophenol of Formula (IX) to produce a compound of Formula (II)

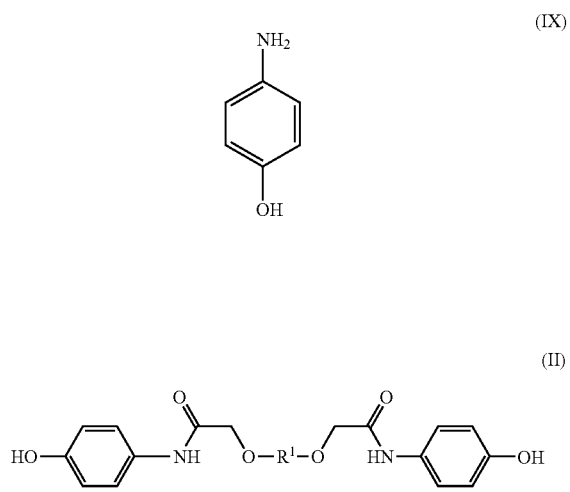

(IX)

(II)

wherein $R^1$ is derived from hydroquinone, methyl hydroquinone, resorcinol or bisphenol A, $R^3$ is hydrogen, and X is bromine.

* * * * *